United States Patent [19]

Schwabe et al.

[11] Patent Number: 4,609,687
[45] Date of Patent: Sep. 2, 1986

[54] MODIFIED FILLERS FOR SILICONE DENTAL PASTES

[75] Inventors: Peter Schwabe; Reiner Voigt, both of Leverkusen, Fed. Rep. of Germany

[73] Assignee: Bayer Aktiengesellschaft, Leverkusen, Fed. Rep. of Germany

[21] Appl. No.: 701,597

[22] Filed: Feb. 14, 1985

[30] Foreign Application Priority Data

Feb. 21, 1984 [DE] Fed. Rep. of Germany ....... 3406233

[51] Int. Cl.$^4$ ................................................ A61K 6/10
[52] U.S. Cl. .................................... 523/109; 106/35; 433/214
[58] Field of Search ................ 523/109; 524/861, 862; 433/214; 106/35, 38.51

[56] References Cited

U.S. PATENT DOCUMENTS 3,591,519  7/1971  Boylan ............................ 106/308 Q
4,007,153  2/1977  Smith ................................. 523/109

Primary Examiner—Lorenzo B. Hayes
Attorney, Agent, or Firm—Sprung Horn Kramer & Woods

[57] ABSTRACT

In the making of a shaped structure by mixing
(a) a cross-linkable organopolysiloxane,
(b) hydrophobic filler particles,
(c) paraffin oil,
(d) a colorant, and
(e) a cross-linking catalyst, the improvement which comprises employing as (b) hydrophobic filler particles of which the surface has been laden with 0.5–5% by weight of paraffin oil. The filler can be present in either or both of a cross-linkable silicone component and a catalyst component; each component can contain other ingredients but will not cure until the two components are brought together. Truer dental impressions are thereby formed.

8 Claims, No Drawings

MODIFIED FILLERS FOR SILICONE DENTAL PASTES

The present invention relates to paraffin-laden fillers for silicone pastes, in particular for kneadable compositions for producing exact impressions of teeth. The silicone pastes are preferably room temperature vulcanizing two-component silicone rubber systems which are known per se and in which two pastes are mixed together, and then undergo crosslinking at room temperature after approx. 2–5 minutes.

Silicone pastes for taking impressions of teeth are widely used. In general, they consist of a silicone oil, which is mixed with fillers and based on a polydimethylsiloxane which possesses terminal hydroxyl groups and, depending on the method of application, is obtainable in various consistencies, and a liquid or pasty curing component which contains a metal salt of a monocarboxylic acid, as a catalyst, and a silicic acid ester as a crosslinking agent.

These two components are mixed with one another before use, and undergo crosslinking at room temperature in the course of 2–5 minutes as a result of a polycondensation reaction. In addition to the crosslinked silicone rubber, this reaction also gives small amounts of alcohol, which slowly diffuse out of the rubber and cause linear shrinkage, which results in inexact impressions.

The linear shrinkage is substantially smaller in the case of the vinyl silicone impression compositions which have only been known for a few years. These compositions consist of two pastes, a basic paste containing silicone oil, filler and crosslinking agent, and a catalyst paste containing silicone oil, filler and catalyst. The silicone oil used is a polydimethylsiloxane which possesses terminal vinyl groups, the crosslinking agent contains the reactive SiH groups, and the catalyst consists of a platinum complex. In these systems, not only does the model possess relatively high dimensional accuracy, but the basic paste and catalyst paste are easier to meter because they have the same viscosity and the mixing ratio of the two pastes has been adjusted to 1:1, and the pastes are completely tasteless and odorless.

Since, in dentistry, various methods are used for taking impressions of toothed, partially toothed and toothless jaws and of mucous membrane, a range of impression compositions of various viscosity classes, for example low-viscosity, medium-viscosity, high-viscosity and kneadable compositions, is required. These compositions consist of a basic paste and a catalyst paste which is specifically adjusted to the required processing time.

While in the case of the low-viscosity, medium-viscosity and high-viscosity compositions the basic paste and the catalyst paste are pressed out of tubes or cartridges in strands of equal length onto a mixing block, and are mixed with a spatula, the basic paste and catalyst paste of the kneadable impression composition is taken out of plastic cans or plastic beakers with appropriately marked measuring spoons, and the lumps of equal size are kneaded with the fingers to give a homogeneous mass. This mass is introduced into an impression tray and then placed in the patient's mouth. After a few minutes, the tray, together with the mass which has crosslinked to form a rubber, can be removed from the patient's mouth. The negative impression of the corresponding jaw situation is then further corrected by using a low-viscosity impression composition, and then filled with an aqueous plaster slurry which, as a plaster model in the hardened state, reproduces the jaw situation.

When the basic and catalyst pastes are removed, and also when the pastes are mixed by kneading with the fingers, it is important that the composition does not stick to the measuring spoons or to the fingers, and/or leave residues behind. Sticking can be prevented by choosing suitable fillers and by adding paraffin oil. While, in the case of the silicone impression compositions which undergo crosslinking by condensation reaction, the adhesive effect can be partially counteracted with talc which is impossible in the case of the vinyl silicone impression compositions which undergo crosslinking by an addition reaction, since talc has an adverse effect on the setting behavior of the compositions. The addition of paraffin oil is also not completely without problems. On the one hand, the amount in the composition has to be 6–8 per cent by weight in order to prevent sticking, while on the other hand some of the paraffin oil is exuded from the pastes as well as from the impressions during storage, that is to say paraffin oil collects in the depressions in the paste surface, or drops of paraffin oil form on the surface of the impressions. The latter effect can, on the one hand, prevent bonding between the kneadable composition after it has hardened and the low-viscosity correcting material if the correction is carried out only after a prolonged period, and, on the other hand, can result in defects in the plaster model. Furthermore, the added paraffin oil reduces the necessary adhesion of the composition to the walls of the impression tray.

These problems are avoided, according to the invention, by the use of paraffin-laden fillers in the pastes. In order to eliminate the tackiness of the pastes, preferably only about 4–5 per cent by weight of paraffin oil is required in the paste, of which, however, 1–2 per cent by weight of paraffin oil is already on the surface of the fillers. Thus, the pastes preferably contain only about 2–4 per cent by weight of free paraffin oil, which in turn possesses affinity to the paraffin-laden filler, and has less tendency to be exuded. In this manner, soft, pliable compositions or impressions having a relatively long shelf life are obtained, that is to say hardly any drops of paraffin oil form in the paste or on the rubber of the impression, so that, even after prolonged storage of the impression, the impression can be satisfactorily corrected and/or a satisfactory plaster model can be prepared.

Furthermore, the adhesion of the composition to the walls of the impression tray is improved.

The invention thus relates to inorganic fillers for pasty silicone compositions, characterized in that the fillers are laden at the surface with 0 5–5% by weight, preferably 1–2.5% by weight, relative to the filler, of paraffin oil.

Preferably, the silicone pastes contain 30 to 90% by weight, in particular 50 to 80% by weight, of the modified fillers according to the invention (relative to the total weight of the paste), if appropriate mixed with conventional non-modified fillers.

The modified fillers according to the invention are preferably used in room temperature-curable dental compositions based on polysiloxane. As already stated at the outset, a distinction is made here between systems which crosslink by addition reaction and those which crosslink by a condensation reaction. Pastes which crosslink by the addition system contain, as essential components,
(a) organopolysiloxanes having two or more vinyl groups in the molecule,
(b) hydrophobic inorganic fillers according to the invention, if appropriate together with conventional inorganic fillers,
(c) organohydrogenopolysiloxanes as crosslinking agents,
(d) a catalyst for accelerating the addition reaction,
(e) paraffin oil and
(f) colorants.

The pastes which undergo crosslinking by the condensation system with a liquid or pasty curing component which consists of a metal salt of a monocarboxylic acid, as a catalyst, and a silicic acid ester as the crosslinking agent contain, as essential components,
(g) organopolysiloxanes having two or more hydroxyl groups in the molecule,
(h) fillers according to the invention, if appropriate in combination with conventional inorganic fillers,
(i) paraffin oil and
(j) colorants.

The kneadable silicone pastes containing fillers according to the invention are distinguished by their long shelf life and freedom from tackiness during mixing of the basic paste and catalyst paste, or of the paste and the curing component. They are suitable for the preparation of exact impressions of teeth because they give a plaster model in which the reproduction is faithful to detail, after the crosslinking paste and the catalyst paste have been thoroughly mixed, introduced into the mouth cavity and compressed therein, the impression has been filled with a plaster slurry, and the latter has hardened to give a model. This good result is achieved because no drops of paraffin oil form on the surface of the impression and interfere with the bond between the preliminary impression, consisting of the kneadable compositions, and the corrective impression, consisting of low-viscosity compositions, and/or falsify the surface of the plaster model.

The starting materials of the abovementioned room temperature-curable pastes are known per se.

Silicone oil (a) is a polydimethylsiloxane which possesses terminal vinyl groups and preferably has a viscosity in the range from 500 to 5,000,000 mPa.s at 20° C.

Examples of suitable fillers (b) are calcium sulphate, diatomaceous earth, talc, calcium carbonate and quartz flours and cristobalite flours which have been modified according to the invention. The particle size of the fillers is preferably between 1 and 25 μm. Fillers which are too finely divided can result in a paste possessing an undesired intrinsic viscosity.

The crosslinking agent (c) is a polydimethylsiloxane the molecule of which has hydrogen atoms on at least two silicon atoms.

The catalyst (d) is, for example, a platinum complex prepared from hexachloroplatinic(IV) acid. These compounds, too, are known per se.

The paraffin oil (e) consists of a mixture of alkanes which is liquid at room temperature and has a viscosity of preferably 120–300 mPa.s, particularly preferably 170–230 mPa.s, at 20° C.

Colorants (f) are employed to differentiate between the basic paste and the catalyst paste, and for monitoring the mixing procedure. Inorganic and organic colored pigments are preferred.

The silicone oil (g) is a polydimethylsiloxane which possesses terminal hydroxyl groups and preferably has a viscosity in the range from 500 to 200,000 mPa.s at 20° C.

The fillers (h), the paraffin oil (i) and the colorants (j) are the same substances as described above under (b), (e) and (f).

The fillers (b) or (h) are coated with paraffin oil in milling apparatuses which are known per se, preferably in ball mills whose walls are coated with, for example, aluminum oxide and whose balls consist of, for example, aluminum oxide (depending on the hardness of the fillers to be coated). The fillers are introduced into the chamber of the ball mill, and 0.5–5, preferably 1–2.5, % by weight of paraffin oil and the balls are added. The closed chamber is allowed to rotate on a roller stand. Of course, the milling process on a suitable apparatus can also be carried out continuously. Thereafter, the free-flowing filler coated with paraffin oil is fractionated by air classification. The amount of paraffin oil to be added is restricted, since the filler forms lumps above the stated limit, and no longer undergoes satisfactory air classification.

The examples which follow, and in which all parts denote parts by weight, illustrate the invention.

EXAMPLE 1

(comparative experiment)

The basic paste was prepared by mixing, in a kneader, 175 parts of polydimethylsiloxane which possessed terminal vinyl groups and had a viscosity of 80,000 mPa.s at 20° C., 50 parts of polydimethylsiloxane which possessed terminal dimethylhydrogenosilyl groups and had a viscosity of 50 mPa.s at 25° C., 650 parts of very fine quartz flour having a mean particle size of about 4 μm, 60 parts of calcium carbonate having a mean particle size of approx. 8 μm, 60 parts of paraffin oil having a viscosity of approx. 180 mPa.s at 20° C. and 5 parts of an inorganic colored pigment.

The catalyst paste was prepared by mixing, in a kneader, 229.8 parts of polydimethylsiloxane which possessed terminal vinyl groups and had a viscosity of 80,000 mPa.s at 20° C., 650 parts of very fine quartz flour having a mean particle size of approx. 4 μm, 60 parts of calcium carbonate having a mean particle size of approx. 8 μm, 60 parts of paraffin oil having a viscosity of 180 mPa.s and 0.2 parts of a complex of platinum and dimethylvinyldisiloxane.

Both pastes are pliable and tack-free and can be readily kneaded, but, on storage for 7 days, paraffin oil collects in the depressions in the surfaces of the two pastes.

15 g of the basic paste and 15 g of the catalyst paste were kneaded with the fingers in the course of 30 seconds to give a homogeneous mass, and this was introduced into the mouth, on an impression tray and under a suitable pressure. The mass hardened in the course of 5 minutes to form an elastomer. After it had been removed from the mouth, washed off with running water and dabbed with wadding, the impression was stored for 24 hours at room temperature. Thereafter, droplets of paraffin oil were formed on the surface of the impression and were transferred to the plaster model (prepared by filling the impression with a plaster slurry consisting of 100 parts of calcium sulphate hemihydrate and 30 parts of water and then storing it for 30 minutes)

in the form of depressions, and hence falsified the plaster model.

In order to produce a corrected impression, a low-viscosity vinyl silicone impression composition was introduced into an impression which had been prepared as described above and stored for 24 hours and which possessed oil drops, and the impression was then introduced into the mouth, under suitable pressure. After removal from the mouth, the composition, which had hardened to an elastomer after 5 minutes, did not exhibit any adhesion to the preliminary impression material at the oil-wet points.

EXAMPLE 2

(according to the invention)

2,000 parts of quartz flour and 30 parts of paraffin oil having a viscosity of 180 mPa.s at 20° C. were mixed for 60 minutes in a ball mill, after which the mixture was subjected to air classification, the fraction having a particle size of less than 25 μm being used to prepare the pastes.

The basic paste was prepared in a kneader by mixing 170 parts of polydimethylsiloxane which possessed terminal vinyl groups and had a viscosity of 80,000 mPa.s at 20° C., 50 parts of polydimethylsiloxane which possessed terminal dimethylhydrogenosilylene groups and had a viscosity of 50 mPa.s at 20° C., 742 parts of the very fine quartz flour laden with paraffin oil, 33 parts of paraffin oil having a viscosity of 180 mPa.s at 20° C. and 5 parts of an organic colored pigment.

The catalyst paste was prepared in a kneader by mixing 230 parts of polydimethylsiloxane which possessed terminat vinyl groups and had a viscosity of 80,000 mPa.s at 20° C., 732 parts of the very fine quartz flour laden with paraffin oil, 37.8 parts of paraffin oil having a viscosity of 180 mPa.s at 20° C. and 0.2 parts of a platinum/siloxane complex.

Both pastes were pliable and tack-free and could be readily kneaded. After storage for 2 months, no exudation of paraffin oil was found.

The two pastes were mixed in a ratio of 1:1, and an impression was produced; after 24 hours, this possessed no oil droplets on the surface. The corrective material adhered satisfactorily, and the plaster model did not exhibit any defects.

EXAMPLE 3

(comparative experiment)

A paste was prepared in a kneader by mixing 210 parts of polydimethylsiloxane which possessed terminal hydroxyl groups and had a viscosity of 50,000 mPa.s at 20° C., 80 parts of paraffin oil having a viscosity of 180 mPa.s at 20° C., 100 parts of calcium carbonate, 600 parts of very fine quartz flour from Example 1, and 10 parts of titanium dioxide.

The paste was pliable and tack-free and could be readily kneaded. On storage for 7 days, however, paraffin oil collected in the depressions in the paste surface.

25 g of paste and 1 g of a curing component consisting of dibutyl-tin dilaurate and tetraethoxysilane (1:1), were kneaded in the course of 30 seconds to give a homogeneous mass which was introduced into the mouth on an impression tray and under a suitable pressure. The mass hardened in the course of 5 minutes to form an elastomer. After it had been removed from the mouth, washed off with running water and dabbed with wadding, the impression was stored for 24 hours at room temperature. Thereafter, droplets of paraffin oil had formed on the surface of the impression and were transferred to the plaster model (prepared by filling the impression with a plaster slurry consisting of 100 parts of calcium sulphate hemihydrate and 30 parts of water and then storing it for 30 minutes) in the form of depressions, and hence falsified the plaster model.

In order to produce a corrected impression, a low-viscosity silicone impression composition was introduced into an impression which had been prepared as described above and stored for 24 hours and which possessed oil drops, and the impression was then introduced into the mouth, under suitable pressure. After removal from the mouth, the composition, which had hardened to an elastomer after 5 minutes, did not exhibit any adhesion to the preliminary impression material at the oil-wet points.

EXAMPLE 4

(according to the invention)

A paste was prepared in a kneader by mixing 220 parts of polydimethylsiloxane which possessed terminal hydroxyl groups and had a viscosity of 50,000 mPa.s at 20° C., 40 parts of paraffin oil having a viscosity of 180 mPa.s, 100 parts of calcium carbonate, 630 parts of very fine quartz flour coated on the surface with paraffin oil as described in Example 2, and 10 parts of titanium dioxide.

The paste was pliable and tack-free and could be readily kneaded. After storage for 2 months, no paraffin oil was found to have separated out.

After the paste had been mixed with the curing component consisting of dibutyl-tin dilaurate and tetraethoxysilane, an impression was produced; this possessed no oil droplets on the surface after 24 hours. The corrective material adhered satisfactorily, and the plaster model had no defects.

It will be understood that the specification and examples are illustrative but not limitative of the present invention and that other embodiments within the spirit and scope of the invention will suggest themselves to those skilled in the art.

What is claimed:

1. In a composition cross-linkable to a shaped structure comprising
    (a) a cross-linkable organopolysiloxane,
    (b) hydrophobic filler particles,
    (c) paraffin oil, and
    (d) a colorant,
the improvement which comprises, as component (b), hydrophobic filler particles of which the surface has been laden with 0.5–5% by weight of paraffin oil.

2. A composition according to claim 1, wherein (a) is an organopolysiloxane having at least two vinyl groups in the molecule, the composition further containing an organohydrogenpolysiloxane as a cross-linking agent.

3. A composition according to claim 1, wherein (a) is an organopolysiloxane having at least two hydroxyl groups in the molecule, the composition further containing a silicic acid ester as a cross-linking agent.

4. In a composition suitable for cross-linking an organopolysiloxane composition to a shaped structure, comprising
    (a) a cross-linkable organopolysiloxane,
    (b) hydrophobic filler particles, and
    (c) a cross-linking catalyst, the improvement which comprises, as component (b), hydrophobic filler particles of which the surface has been laden with 0.5-5% by weight of paraffin oil.

5. In a method for making a shaped structure comprising mixing (a) a cross-linkable organopolysiloxane, (b) hydrophobic filler particles, (c) paraffin oil, (d) a colorant, and (e) a cross-linking catalyst and forming the mixture into a desired shape, the improvement which comprises, as component (b), hydrophobic filler particles of which the surface has been laden with 0.5-5% by weight of paraffin oil.

6. A composition according to claim 1, wherein said organopolysiloxane is a polydimethylsiloxane having terminal vinyl groups and having a viscosity of 500 to 5,000,000 mPa.s at 20° C.

7. A composition according to claim 1, wherein the filler is selected from the group consisting of calcium sulphate, diatomaceous earth, talc, calcium carbonate, quartz flours and critobalite fluors.

8. A composition according to claim 4, wherein the catalyst is a platinum prepared from hexachloroplatinic (IV) acid.

* * * * *